United States Patent [19]

Adams

[11] Patent Number: 5,235,979

[45] Date of Patent: Aug. 17, 1993

[54] DUAL BATTERY SYSTEM FOR IMPLANTABLE DEFIBRILLATOR

[75] Inventor: Theodore P. Adams, Edina, Minn.

[73] Assignee: Angeion, Corporation, Plymouth, Minn.

[21] Appl. No.: 913,626

[22] Filed: Jul. 16, 1992

Related U.S. Application Data

[63] Continuation of Ser. No. 670,188, Mar. 15, 1991, abandoned.

[51] Int. Cl.$^5$ .............................................. A61N 1/39
[52] U.S. Cl. ....................................................... 607/5
[58] Field of Search ........ 128/419 D, 419 PG, 419 PS

[56] References Cited

U.S. PATENT DOCUMENTS

| | | | |
|---|---|---|---|
| 3,258,013 | 6/1966 | Druz | 128/419 D |
| 3,865,101 | 2/1975 | Saper et al. | 128/419 D |
| 4,041,956 | 8/1977 | Purdy et al. | 128/419 P |
| 4,096,856 | 6/1978 | Smith et al. | 128/419 D |
| 4,096,866 | 6/1978 | Fischell | 128/419 PG |
| 4,323,075 | 4/1982 | Langer | 128/419 D |
| 4,635,639 | 1/1987 | Hakala et al. | 128/419 D |
| 4,787,389 | 11/1988 | Tarjan | 128/419 PG |
| 4,827,936 | 5/1989 | Pless et al. | 128/419 D |

*Primary Examiner*—Kyle L. Howell
*Assistant Examiner*—Kennedy J. Schaetzle
*Attorney, Agent, or Firm*—Patterson & Keough

[57] ABSTRACT

An implantable defibrillator comprising a first implantable energy source connected to an implantable monitoring circuit means and a second implantable energy source having a predetermined different energy output than said first implantable energy source connected to an implantable inverter/output circuit means. The implantable monitoring circuit is powered by the first implantable energy source and the implantable inverter/output circuit is powered by the second implantable energy source.

7 Claims, 1 Drawing Sheet

DUAL BATTERY SYSTEM FOR IMPLANTABLE DEFIBRILLATOR

This application is a continuation of application Ser. No. 07/670,188, filed Mar. 15, 1991, now abandoned.

BACKGROUND OF THE INVENTION

1. Field of the Invention

The present invention pertains to a defibrillator, and more particularly, pertains to a dual battery system for use with an implantable defibrillator. Two batteries, each having physically and electrically correct parameters and qualities, are used to power the monitoring and energy delivery systems of an implantable defibrillator.

2. Description of the Prior Art

Implantable defibrillators have several unique battery requirements, vis-a-vis other implantable products. This application demands a battery with the following general characteristics: very high reliability, highest possible energy density (i.e., small size), extremely low self-discharge rate (i.e., long shelf life), very high current capability, high operating voltage, and capable of being sealed (i.e., no gas or liquid venting).

Some of these parameters have some measure of mutual exclusivity, making it difficult to optimize the battery or electronics without making compromises to the design of an implantable defibrillator. In its monitoring mode, the defibrillator requires the battery to deliver continuous currents in the range of only 10 to 30 microamps, while in its defibrillation mode, the same battery must deliver currents in the range of one to two amps, some five orders of magnitude greater.

The longevity of the implanted device and the number of shocks it is capable of delivering is strictly dependant on the remaining battery capacity at any given time. As the device ages, its ability to deliver an adequate number of defibrillating shocks declines as the battery is depleted by the monitoring electronics. Similarly, if a patient receives a large number of shocks soon after implant, the remaining monitoring life is reduced. Thus, it is difficult to assess the condition of the battery and its remaining useful life after it has been in use for a period of time.

A further disadvantage of the single battery configuration is that the ideal voltage requirements for the monitoring and output functions are opposite. For the monitoring function, it is desirable to use the lowest possible voltage that the circuits can operate reliably with in order to conserve energy. This is typically in the order of 1.5 to 3.0 volts. On the other hand, the output circuit works most efficiently with the highest possible voltage, including voltages up to 800 volts. The current defibrillators have compromised by making a single battery from two lithium vanadium pentoxide cells in series to produce about 6 volts. The battery voltage must be elevated via an inverter circuit to the firing voltage of about 750 volts. The net result is that power is wasted in both the monitoring and output circuits since the monitoring circuit that requires only 2-3 volts must operate from a 6 volt source, and the output circuit whose efficiency is a function of the supply voltage must operate from the relatively low 6 volt source.

The present invention overcomes the deficiencies of the prior art by providing a dual battery system for an implantable defibrillator where a separate battery is provided for the monitoring circuit and for the energy output circuit.

SUMMARY OF THE INVENTION

The general purpose of the present invention described herein involves the use of two separate battery power sources for an implantable defibrillator, each having optimized characteristics for monitoring and for shock energy delivery functions, as opposed to current technology, wherein a single power source is used for both functions. In a device utilizing the invented power source scheme, the monitoring function is supplied by a conventional pacemaker power source, such as a lithium iodide battery, which is optimized for long life at very low current levels. The output energy is supplied by a separate battery, such as a lithium vanadium pentoxide battery, which is optimized for high current drain capability and low self-discharge for long shelf life.

With such a power source configuration, the monitoring life of the defibrillator is independent of the number of shocks delivered, and the end of the monitoring battery life is highly predictable based on steady state current drain calculations. The life of the output power source battery is also amenable to calculation based upon the number of energy levels of previously delivered shocks.

The major advantage of this configuration of battery power sources is that each battery voltage can be optimized for the particular circuit wherein it is used. The monitoring battery is of a relatively low voltage source ranging from 1.5 to 3.0 volts typically, whereas the output voltage source would be as high as battery chemistry and battery packaging efficiencies allow, and typically ranging from 6 to 18 volts.

According to one embodiment of the present invention, there is provided a dual battery system for use with an implantable defibrillator. A monitoring circuit is powered by an appropriate electrically and physically sized battery. Another appropriate electrically and physically sized battery powers an output circuit which also includes an inverter. The monitoring circuit provides control of the inverter/output circuit and is also connected to a defibrillator implanted within a person. The output circuit also connects to the defibrillator for stimulation of the heart organ.

One significant aspect and feature of the present invention is a dual battery supply for an implantable defibrillator.

Another significant aspect and feature of the present invention is greater longevity provided for by lower energy drain from the monitoring circuit.

Yet another significant aspect and feature of the present invention is greater efficiency in the high voltage inverter output circuit so that a smaller battery may provide an increased number of shocks.

Still another significant aspect and feature of the present invention is a lower current requirement from the output battery, whereby a greater number of battery chemistry options are available.

An additional significant aspect and feature of the present invention is the reduction in the complexity of the inverter circuit.

One other significant aspect and feature of the present invention is simplified circuit design by lessening the risk of high internal currents causing interference to other parts of the circuit.

Another significant aspect and feature of the present invention is the use of rechargeable batteries.

Having thus described one embodiment of the present invention, it is the principal object hereof to provide a dual battery system for an implantable defibrillator.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
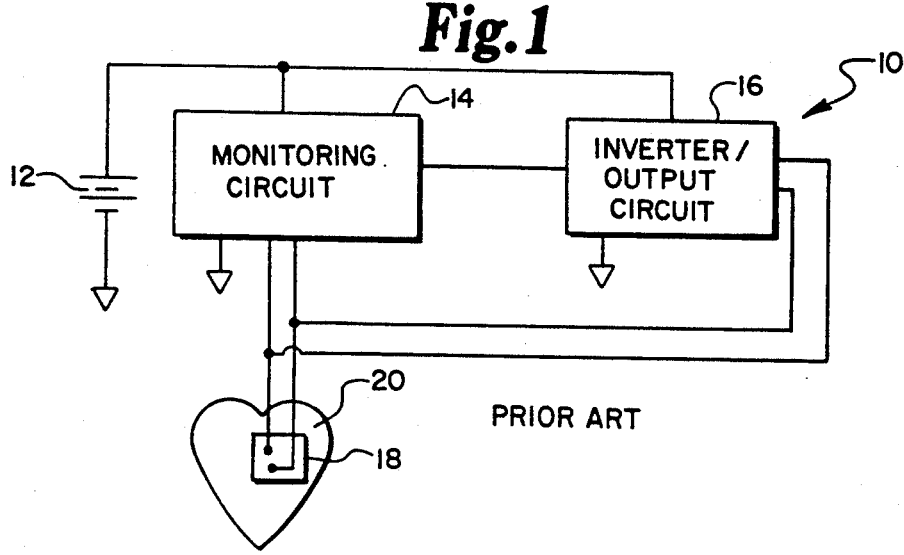
FIG. 1 illustrates the prior art.

FIG. 1 illustrates the prior art implantable defibrillator system 10 including a single battery 12, which provides power both to a monitoring circuit 14 and an inverter/output circuit 16 simultaneously. The monitoring circuit 14 and the inverter/output circuit 16 are interconnected to each other, and to a defibrillator head 18 located on a heart 20. As discussed in the prior art, electrical size of the single battery 12 may be excessive with relation to the circuit requirements of the monitoring circuit 14, and marginal or even somewhat lacking in electrical size in relation to the circuit requirements of the inverter/output circuit 16.

Figure 2:
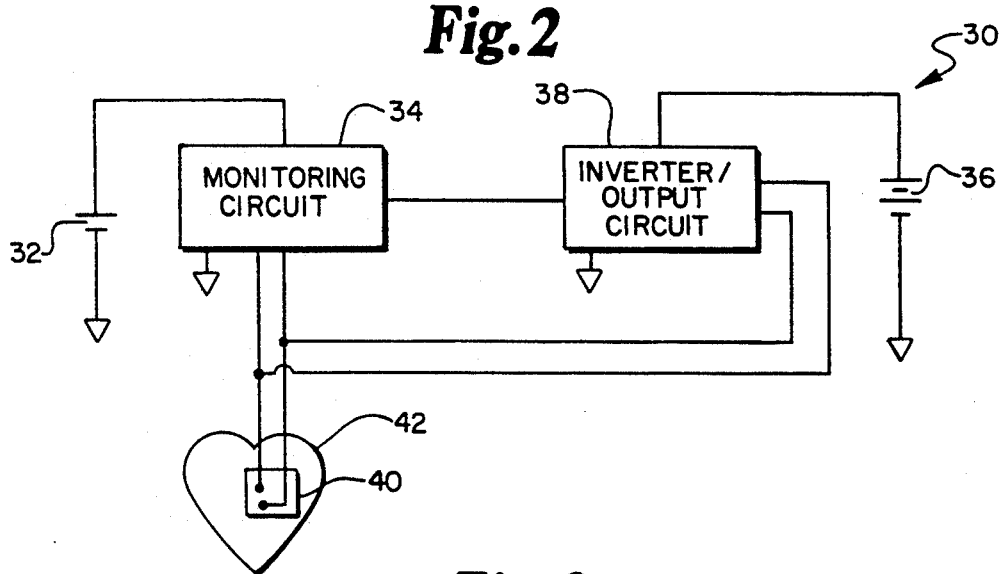
FIG. 2 illustrates a block diagram of the present invention.

FIG. 2 illustrates a block diagram of the dual battery system 30 for an implantable defibrillator. A battery 32 of appropriate voltage and physical size connects to and powers a monitoring circuit 34 only. Another battery 36 of appropriate voltage and physical size connects to and powers the inverter/output circuit 38 only. The monitoring circuit 34 and the inverter/output circuit 38 each connect to a defibrillator head 40 on a heart 42. The monitoring circuit 34 also connects to and triggers the inverter/output circuit 38. The batteries 32 and 36 are optimally sized electrically and physically to provide for the most efficient operation.

The mode of operation of FIG. 2 is dependent upon the monitoring circuit 34 and the output circuit 38 for the defibrillator.

Figure 3:
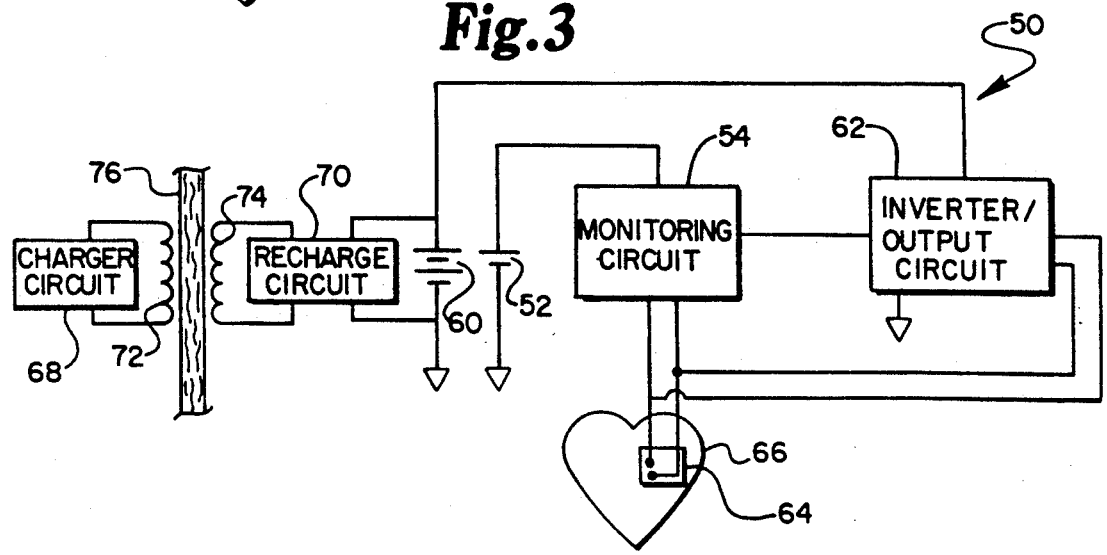
FIG. 3 illustrates a block diagram of the present invention using a rechargeable inverter/output battery.

FIG. 3 illustrates a dual battery system 50 for an implantable defibrillator where the batteries are rechargeable. A battery 52 of appropriate voltage and physical size connects to and powers a monitoring circuit 54 only. Another battery 60, which is rechargeable and of appropriate voltage and physical size connects to and powers the inverter/output circuit 62 only. Charging of the battery 60 occurs by a radio frequency link between an external charger circuit 68 and an implanted recharge circuit 70. A coil 72 connects with the external charger circuit 68 and transmits RF energy from the coil 72 through the epidermis 76 where it is received by an implanted coil 74. The coil 74 supplies RF energy to the recharge circuit 70 so that the battery 60 may be charged.

In operation, as in FIG. 2, the monitoring circuit 54 and the inverter/output circuit 62 each connect to a defibrillator head 64 on a heart 66. The monitoring circuit 54 also connects to and triggers the inverter/output circuit 62. The batteries 52 and 60 are optionally sized electrically and physically to provide for the most efficient operation. In this configuration, the device has a finite and predictable monitoring life based upon the capacity of the primary pacing battery 52, and an infinite life for the output power surface battery 60 based on a theoretically perfect secondary rechargeable battery. Optionally, the battery 52 which powers the monitoring circuit 54 can also be rechargeable and would also include another similar RF charging link as used for the rechargeable battery 60.

Various modifications can be made to the present invention without departing from the apparent scope hereof.

I claim:

1. An implantable defibrillator comprising:
   a. a first implantable energy source connected to an implantable monitoring circuit means, said implantable monitoring circuit means being powered by said first implantable energy source; and,
   b. a second implantable energy source having a predetermined different energy output than said first implantable energy source, connected to an implantable inverter/output circuit means, said implantable inverter/output circuit means being powered by said second implantable energy source.

2. The implantable defibrillator according to claim 1 wherein said first implantable energy source is a relatively low voltage source, and wherein said second implantable energy source is a relatively high voltage source.

3. The implantable defibrillator according to claim 2 wherein said relatively low voltage source is 1.5 to 3.0 volt battery.

4. The implantable defibrillator of claim 3 wherein said battery is a lithium iodide battery.

5. The implantable battery defibrillator according to claim 2 wherein said relatively high voltage source is a 6 to 18 volt battery.

6. The implantable defibrillator according to claim 5 wherein said battery is selected from the group consisting of a lithium vanadium pentoxide battery, silver lithium vanadium pentoxide or a lithium vanadium oxide chemistry.

7. The implantable defibrillator of claim 1 wherein said implantable monitoring circuit means is electrically connected to said inverter/output circuit means so as to automatically trigger an output from said inverter/output circuit means.

* * * * *

REEXAMINATION CERTIFICATE (2422nd)

United States Patent [19]

Adams

[11] B1 5,235,979

[45] Certificate Issued  Nov. 1, 1994

[54] DUAL BATTERY SYSTEM FOR IMPLANTABLE DEFIBRILLATOR

[75] Inventor: Theodore P. Adams, Edina, Minn.

[73] Assignee: Angeion Corp., Plymouth, Minn.

Reexamination Request:
No. 90/003,242, Nov. 3, 1993

Reexamination Certificate for:
Patent No.: 5,235,979
Issued: Aug. 17, 1993
Appl. No.: 913,626
Filed: Jul. 16, 1992

Related U.S. Application Data

[63] Continuation of Ser. No. 670,188, Mar. 15, 1991, abandoned.

[51] Int. Cl.⁵ ............................................. A61N 1/39
[52] U.S. Cl. ..................................................... 607/5
[58] Field of Search .................. 607/5, 4, 36, 34, 29, 607/2

[56] References Cited

U.S. PATENT DOCUMENTS

| | | |
|---|---|---|
| 3,258,013 | 6/1966 | Druz . |
| 3,822,707 | 7/1974 | Adducci et al. ............... 607/36 |
| 3,865,101 | 2/1975 | Saper et al. . |
| 4,041,956 | 8/1977 | Purdy et al. . |
| 4,096,856 | 6/1978 | Smith et al. . |
| 4,096,866 | 6/1978 | Fischell . |
| 4,323,075 | 4/1982 | Langer . |
| 4,548,209 | 10/1985 | Wielders et al. . |
| 4,635,639 | 1/1987 | Hakala et al. . |
| 4,787,389 | 11/1988 | Tarjan . |
| 4,827,936 | 5/1989 | Pless et al. . |

OTHER PUBLICATIONS

Troup, "Implantable Cardioverters and Defibrillators," *Current Problems in Cardiology*, vol. XIV, No. 12, Dec. 1989, pp. 703, 704.

*Primary Examiner*—K. L. Howell

[57] ABSTRACT

An implantable defibrillator comprising a first implantable energy source connected to an implantable monitoring circuit means and a second implantable energy source having a predetermined different energy output than said first implantable energy source connected to an implantable inverter/output circuit means. The implantable monitoring circuit is powered by the first implantable energy source and the implantable inverter/output circuit is powered by the second implantable energy source.

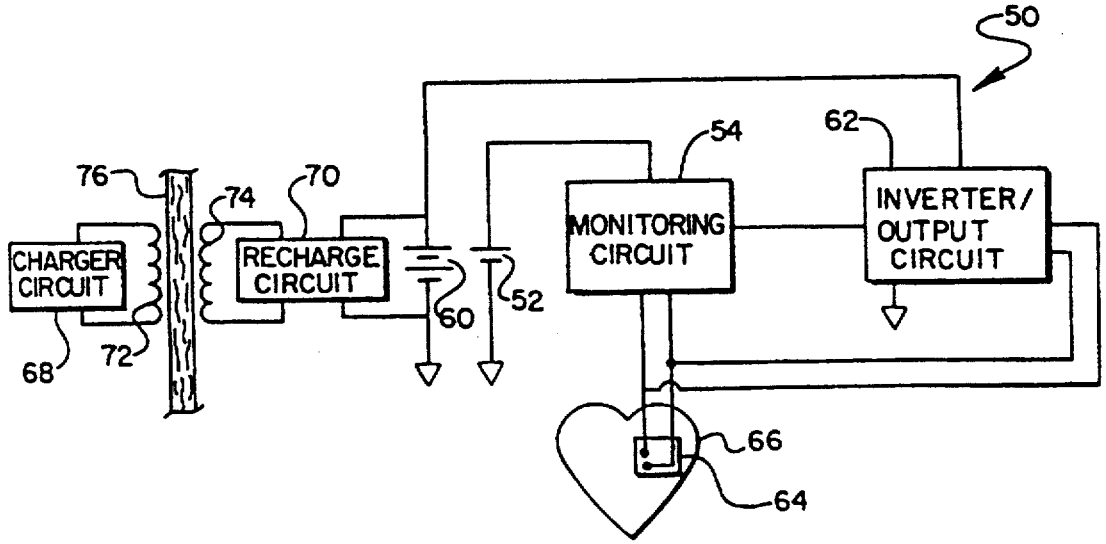

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–7 are cancelled.

* * * * *